United States Patent
Perkins et al.

(10) Patent No.: US 11,672,645 B2
(45) Date of Patent: Jun. 13, 2023

(54) SINGLE MULTIBRANCH STENT DEVICE ASSEMBLY AND METHOD

(71) Applicant: Medtronic Vascular, Inc., Santa Rosa, CA (US)

(72) Inventors: Keith Perkins, Santa Rosa, CA (US); Zachary Borglin, Santa Rosa, CA (US); Mark Stiger, Santa Rosa, CA (US); Julie Benton, Santa Rosa, CA (US); Steven Claessens, Santa Rosa, CA (US); Travis Rowe, Santa Rosa, CA (US); Mark Young, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 71 days.

(21) Appl. No.: 17/380,824

(22) Filed: Jul. 20, 2021

(65) Prior Publication Data

US 2021/0346145 A1 Nov. 11, 2021

Related U.S. Application Data

(62) Division of application No. 16/502,462, filed on Jul. 3, 2019, now Pat. No. 11,096,775.

(51) Int. Cl.
*A61F 2/95* (2013.01)
*A61F 2/07* (2013.01)
(Continued)

(52) U.S. Cl.
CPC ............... *A61F 2/07* (2013.01); *A61F 2/954* (2013.01); *A61F 2002/061* (2013.01); *A61M 25/09* (2013.01)

(58) Field of Classification Search
CPC .. A61F 2/07; A61F 2/954; A61F 2/962; A61F 2/966; A61F 2/9662; A61F 2/97;
(Continued)

(56) References Cited

U.S. PATENT DOCUMENTS 8,545,549 B2 10/2013 Hartley et al.
8,702,791 B2 4/2014 Kelly
(Continued)

FOREIGN PATENT DOCUMENTS

EP 2525742 B1 11/2012
EP 2574306 A1 4/2013
(Continued)

OTHER PUBLICATIONS

PCT/US2020/023170, The International Search Report and the Written Opinion of the International Searching Authority, dated Jun. 30, 2020, 12 pages.
(Continued)

*Primary Examiner* — Erich G Herbermann
(74) *Attorney, Agent, or Firm* — Brooks Kushman P.C.

(57) ABSTRACT

The techniques of this disclosure generally relate to an assembly including a single multibranch stent device. The single multibranch stent device includes a main body, a proximal coupling extending radially from the main body, and a distal coupling extending radially from the main body. The main body, the proximal coupling, and the distal coupling are permanently coupled to one another and the single multibranch stent device is a single piece. By forming the single multibranch stent device as a single piece, the single multibranch stent device can be deployed in a single deployment thus simplifying the deployment procedure.

25 Claims, 15 Drawing Sheets

(51) Int. Cl.
  *A61F 2/954* (2013.01)
  *A61F 2/06* (2013.01)
  *A61M 25/09* (2006.01)

(58) Field of Classification Search
  CPC ........ A61F 2002/061; A61F 2002/9623; A61F 2002/9665; A61F 2002/067; A61F 2002/075; A61F 2002/821; A61F 2002/8486; A61F 2210/0014; A61F 2220/0033; A61F 2220/0075; A61M 25/09
  See application file for complete search history.

(56) References Cited

U.S. PATENT DOCUMENTS

| | | | |
|---|---|---|---|
| 8,734,504 B2 | 5/2014 | Kelly | |
| 9,011,517 B2 | 4/2015 | Hartley et al. | |
| 9,101,456 B2 | 8/2015 | Hartley et al. | |
| 9,283,068 B2 | 3/2016 | Kelly | |
| 9,393,102 B2 | 7/2016 | Kelly | |
| 9,592,112 B2 | 3/2017 | Arbefeuille et al. | |
| 9,839,542 B2 | 12/2017 | Bruszewski et al. | |
| 9,861,505 B2 | 1/2018 | Khoury | |
| 9,949,818 B2 | 4/2018 | Kelly | |
| 9,980,832 B2 | 5/2018 | Kelly | |
| 9,993,330 B2 | 6/2018 | Roeder | |
| 10,231,822 B2 | 3/2019 | Hartley | |
| 2002/0099441 A1 | 7/2002 | Dehdashtian | |
| 2006/0155363 A1 | 7/2006 | LaDuca et al. | |
| 2009/0306763 A1 | 12/2009 | Roeder et al. | |
| 2011/0196477 A1 | 8/2011 | Ganesan et al. | |
| 2011/0238160 A1 | 9/2011 | Molony | |
| 2012/0123526 A1* | 5/2012 | Ko ........................ | A61F 2/856 623/1.35 |
| 2012/0271401 A1 | 10/2012 | Bruszewski et al. | |
| 2013/0274861 A1 | 10/2013 | Kelly | |
| 2016/0287376 A1 | 10/2016 | Kelly | |
| 2016/0324626 A1 | 11/2016 | Kelly | |
| 2016/0367353 A1 | 12/2016 | Kelly | |
| 2017/0296324 A1 | 10/2017 | Argentine | |
| 2018/0071077 A1 | 3/2018 | Argentine et al. | |
| 2018/0153677 A1 | 6/2018 | Perkins et al. | |
| 2018/0235786 A1 | 8/2018 | Kelly | |
| 2018/0243076 A1 | 8/2018 | Greenberg et al. | |
| 2018/0325653 A1 | 11/2018 | Kelly | |
| 2019/0365523 A1 | 12/2019 | Haulon et al. | |

FOREIGN PATENT DOCUMENTS

| | | |
|---|---|---|
| EP | 3448313 B1 | 4/2020 |
| WO | 2014163957 A1 | 10/2014 |
| WO | 2019245624 A1 | 12/2019 |

OTHER PUBLICATIONS

PCT/US2020/023176, The International Search Report and the Written Opinion of the International Searching Authority, dated Jun. 19, 2020, 15 pages.
U.S. Appl. No. 16/585,722, of Keith Perkins et al., titled "Docking Graft for Placement of Parallel Distally Extending Grafts Assembly and Method", filed Sep. 27, 2019.
U.S. Appl. No. 16/585,768, of Keith Perkins et al., titled "Supra Aortic Access Trifurcated Modular Stent Assembly and Method", filed Sep. 27, 2019.
U.S. Appl. No. 16/527,769, of Keith Perkins et al., titled "Modular Multibranch Stent Assembly and Method", filed Jul. 31, 2019.
U.S. Appl. No. 16/554,803, of Ashish Dhawan et al., titled "Use of Multiple Charged Ionic Compounds Derived From Polyamines for Waste Water Clarification", filed Aug. 29, 2019.
U.S. Appl. No. 16/554,813, of Keith Perkins et al., titled "Modular Multibranch Stent Assembly and Method", filed Aug. 29, 2019.
U.S. Appl. No. 15/830,221 of Keith Perkins et al., titled "Modular Aortic Arch Prosthetic Assembly and Method of Use Thereof", filed Dec. 4, 2017.
U.S. Appl. No. 16/367,889 of Keith Perkins et al., titled "Modular Stent Device for Multiple Vessels and Method", filed Mar. 28, 2019.
U.S. Appl. No. 16/367,906, of Keith Perkins et al., titled Supra Aortic Access Modular Stent Assembly and Method, filed Mar. 28, 2019.
U.S. Appl. No. 16/367,922 of Keith Perkins et al., titled Femoral Aortic Access Modular Stent Assembly and Method, filed Mar. 28, 2019.
U.S. Appl. No. 62/430,218 of Keith Perkins et al., titled "Modular Aortic Arch Prosthetic Assembly and Method of Use Thereof", filed Dec. 5, 2016.
U.S. Appl. No. 62/687,087 of Keith Perkins et al., titled "Modular Stent Device for Multiple Vessels", filed Jun. 19, 2018.
M. Lachat, Nexus aortic arch stentgraft: Mid-term results, Leipzig Interventional Course 2017, UniversitatsSpital Zurich, Jan. 24-27, 2017, pp. 1-30, www.leipzig-interventional-course.com.
Jae Woong Lim et al., "Totally endocascular aortic arch repair by branched stent graft placement", Journal of Wascular Surgery Cases, Dec. 2015, pp. 279-282, vol. 1, No. 4.
W. Anthony Lee, MD., "The Bolton Medical BranchedThoracic Stent-Graft", Sponsored by Bolton Medical, Inc., pp. 1-6.
Michael D. Dake et al., "Thoracic Branch Endoprosthesis: Early Case Experience and the Clinical Trial", Supplemental to Endovascular Today, Mar. 2017, pp. 21-24, vol. 16, No. 3.
Augusto D'Onofrio et al., "Endovascular Treatment of aortic arch aneurysm with a single-branched double-stage stent graft", The Journal of Thoracic and Cardiovascular Surgery, Jul. 11, 2017, pp. e75-e77, Voume 154, No. 5.
Joseph Anderson, "Complete endovascular debranching of the aortic arch: A report of two cases", Vascular, Jul. 11, 2014, pp. 1-7, http://vas.sagepub.com/content/early/2014/07/11/1708538114542174, SAGE Publications.
Ciro Ferrer et al., "Endovascular repair of aortic arch disease with double inner branched thoracic stent graft: the Bolton perspective", The Journal of Cardiovascular Surgery, Aug. 2018, pp. 547-553, vol. 59 No.4.
Stephan Haulon et al., "Global experience with an inner branched arch endograft", The Journal of Thoracic and Cardiovascular Surgery, 2014, pp. 1709-1716, vol. 148 No.4.
Chen Huang et al., "Application of Unibody Single-Branch Endografts in Stanford Type B Dissections with Primary Entry Tear Adjacent to the Left Subclavian Artery: A Computed TomographyeBased Planning Study", Annals for Vascular Surgery, Aug. 2015, pp. 1174-1180, vol. 29 No.6.
Himanshu J. Patel et al., "Branched Endovascular Therapy of the Distal Aortic Arch: Preliminary Results of the Feasibility Multicenter Trial of the Gore Thoracic Branch Endoprosthesis", Branched Aortic Arch Tevar Trial, The Society of Thoracic Surgeons, Mar. 22, 2016, pp. 1190-1198, Elsevier Ltd.
Vincent Riambau et al., "Application of the Bolton Relay Device for Thoracic Endografting In or Near the Aortic Arch", Aorta, Feb. 2015, pp. 16-24, vol. 3 Issue 1, Science International Corp., http://aorta.scienceinternational.org.
R. Spear et al., "Editor's Choice e Subsequent Results for Arch Aneurysm Repair with Inner Branched Endografts", Arch Aneurysm Endovascular Repair, Dec. 8, 2015, pp. 380-385., European Society for Vascular Surgery, Elsevier Ltd.
R. Spear et al., "Complex endovascular repair of postdissection arch and thoracoabdominal aneurysms", Society for Vascular Surgery, Journal of Vascular Surgery, Sep. 5, 2017, pp. 1-8, Elsevier Inc.
R. Spear et al., "Total Endovascular Treatment of Aortic Arch Disease Using an Arch Endograft With 3 Inner Branches", Journal of Endovascular Therapy, 2017, pp. 534-538, vol. 24(4), Sage Publications.
Zhong Gao Wang, "Single-Branch Endograft for Treating Stanford Type B Aortic Dissections With Entry Tears in Proximity to the Left Subclavian Artery", J Endovasc Ther, 2005, pp. 588-593, International Society of Endovascular Specialists.
International Search Report, Application No. PCT/US2019/024676, dated Jun. 17, 2019, pp. 1-14.

(56) References Cited

OTHER PUBLICATIONS

PCT/US2020/039169, The International Search Report and the Written Opinion of the International Searching Authority, dated Oct. 5, 2020, 16 pages.
PCT/US2020/044833, The International Search Report and the Written Opinion of the International Searching Authority, dated Nov. 16, 2020, 11 pages.

* cited by examiner

SINGLE MULTIBRANCH STENT DEVICE ASSEMBLY AND METHOD

RELATED APPLICATIONS

This application is a divisional of pending U.S. patent application Ser. No. 16/502,462, entitled "SINGLE MULTIBRANCH STENT DEVICE ASSEMBLY AND METHOD", filed Jul. 3, 2019, and issued as U.S. Pat. No. 11,096,775 on Aug. 24, 2021, which is incorporated herein by reference in its entirety.

FIELD

The present technology is generally related to an intra-vascular device and method. More particularly, the present application relates to a device for treatment of intra-vascular diseases.

BACKGROUND

Aneurysms, dissections, penetrating ulcers, intramural hematomas and/or transections may occur in blood vessels, and most typically occur in the aorta and peripheral arteries. The diseased region of the aorta may extend into areas having vessel bifurcations or segments of the aorta from which smaller "branch" arteries extend.

The diseased region of the aorta can be bypassed by use of a stent-graft placed inside the vessel spanning the diseased portion of the aorta, to seal off the diseased portion from further exposure to blood flowing through the aorta.

The use of stent-grafts to internally bypass the diseased portion of the aorta is not without challenges. In particular, care must be taken so that critical branch arteries are not covered or occluded by the stent-graft yet the stent-graft must seal against the aorta wall and provide a flow conduit for blood to flow past the diseased portion.

SUMMARY

The techniques of this disclosure generally relate to an assembly including a single multibranch stent device. The single multibranch stent device includes a main body, a proximal coupling extending radially from the main body, and a distal coupling extending radially from the main body. The main body, the proximal coupling, and the distal coupling are permanently coupled to one another and the single multibranch stent device is a single piece. By forming the single multibranch stent device as a single piece, the single multibranch stent device can be deployed in a single deployment thus simplifying the deployment procedure.

In one aspect, the present disclosure provides an assembly comprising a single multibranch stent device. The single multibranch stent device includes a main body, a proximal coupling extending from the main body, and a distal coupling extending from the main body. The proximal coupling is configured to perfuse the brachiocephalic artery. The distal coupling is configured to perfuse an aortic branch vessel distal of the brachiocephalic artery. The main body, the proximal coupling, and the distal coupling are a single piece.

In another aspect, the present disclosure provides a method including deploying a single multibranch stent device. The deployment includes deploying a main body within the aorta, perfusing the brachiocephalic artery through a proximal coupling extending radially from the main body, and perfusing an aortic branch vessel distal of the brachiocephalic artery through a distal coupling extending radially from the main body. The main body, the proximal coupling, and the distal coupling are permanently coupled to one another.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
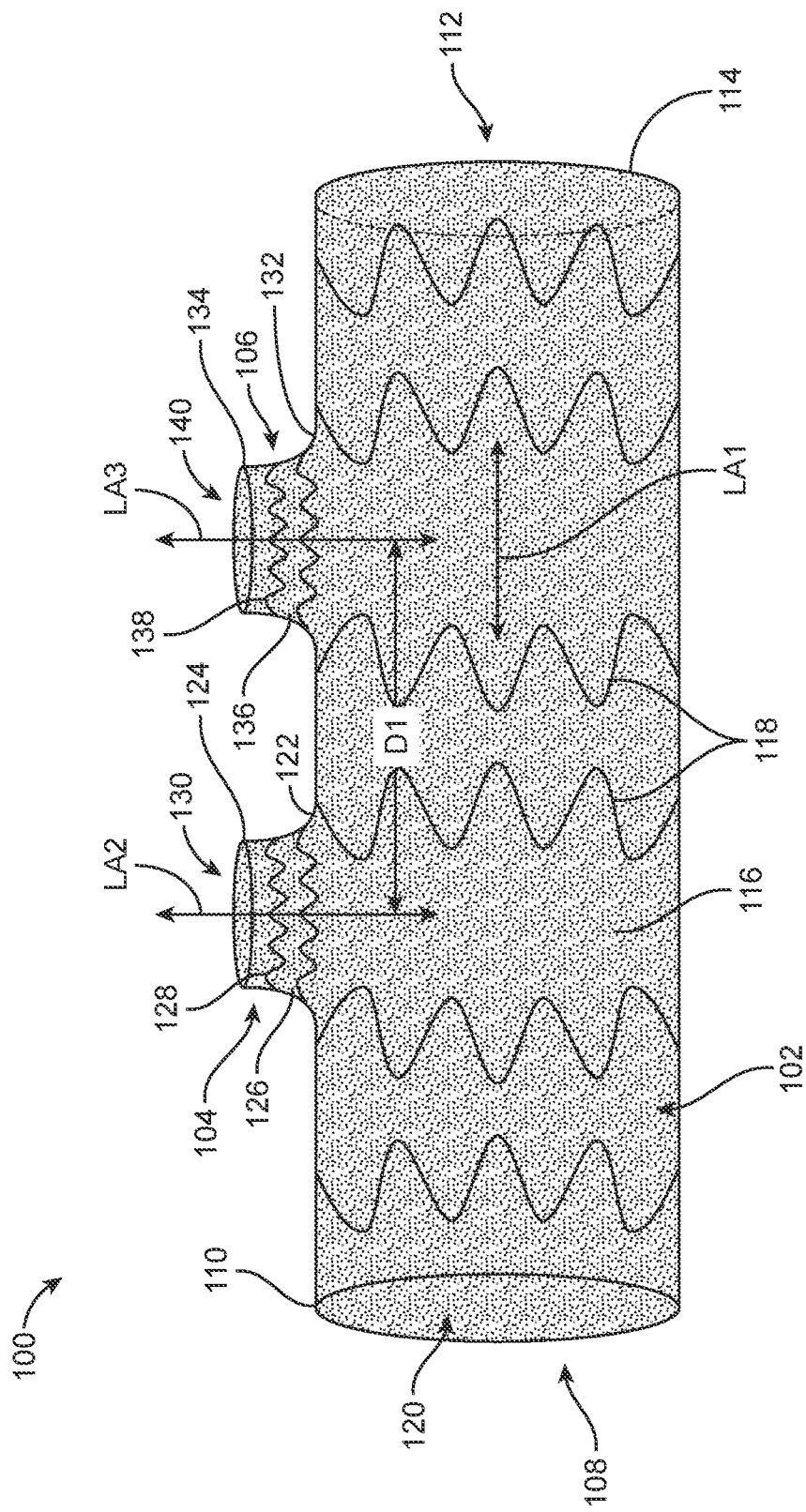
FIG. 1 is a side perspective view of a single multibranch stent device in accordance with one embodiment.

FIG. 1 is a side perspective view of a single multibranch stent device 100 in accordance with one embodiment. Single multibranch stent device 100, sometimes called a prosthesis or aortic arch prosthesis, includes a main body 102, a proximal coupling 104, and a distal coupling 106. Proximal coupling 104 and distal coupling 106 are sometimes called volcanoes.

In accordance with this embodiment, main body 102 includes a main body proximal opening 108 at a proximal end 110 of main body 102. Main body 102 further includes a main body distal opening 112 at a distal end 114 of main body 102.

As used herein, the proximal end of a prosthesis such as single multibranch stent device 100 is the end closest to the heart via the path of blood flow whereas the distal end is the end furthest away from the heart during deployment. In contrast and of note, the distal end of the catheter is usually identified to the end that is farthest from the operator/handle while the proximal end of the catheter is the end nearest the operator/handle.

For purposes of clarity of discussion, as used herein, the distal end of the catheter is the end that is farthest from the operator (the end furthest from the handle) while the distal end of single multibranch stent device 100 is the end nearest the operator (the end nearest the handle), i.e., the distal end of the catheter and the proximal end of single multibranch stent device 100 are the ends furthest from the handle while the proximal end of the catheter and the distal end of single multibranch stent device 100 are the ends nearest the handle. However, those of skill in the art will understand that depending upon the access location, single multibranch stent device 100 and the delivery system descriptions may be consistent or opposite in actual usage.

Main body 102 includes graft material 116 and one or more circumferential stents 118 coupled to graft material 116. Graft material 116 may be any suitable graft material, for example and not limited to, woven polyester, DACRON® material, expanded polytetrafluoroethylene, polyurethane, silicone, electro spun materials, or other suitable materials.

Circumferential stents 118 may be coupled to graft material 116 using stitching or other means. In the embodiment shown in FIG. 1, circumferential stents 118 are coupled to an outside surface of graft material 116. However, circumferential stents 118 may alternatively be coupled to an inside surface of graft material 116.

Although shown with a particular number of circumferential stents 118, in light of this disclosure, those of skill in the art will understand that main body 102 may include a greater or smaller number of stents 118, e.g., depending upon the desired length of main body 102 and/or the intended application thereof.

Circumferential stents 118 may be any stent material or configuration. As shown, circumferential stents 118, e.g., self-expanding members, are preferably made from a shape memory material, such as nickel-titanium alloy (nitinol), and are formed into a zig-zag configuration. The configuration of circumferential stents 118 is merely exemplary, and circumferential stents 118 may have any suitable configuration, including but not limiting to a continuous or non-continuous helical configuration. In another embodiment, circumferential stents 118 are balloon expandable stents.

Further, main body 102 includes a longitudinal axis LA1. A lumen 120 is defined by graft material 116, and generally by main body 102. Lumen 120 extends generally parallel to longitudinal axis LA1 and between proximal opening 108 and distal opening 112 of main body 102. Graft material 116 is cylindrical having a substantially uniform diameter in this embodiment. However, in other embodiments, graft material 116 varies in diameter.

Proximal coupling 104 extends radially from main body 102. Proximal coupling 104 corresponds with an opening in main body 102. Proximal coupling 104 is generally frustoconically shaped and includes a base 122 and a top 124. A circumference of base 122 is greater than a circumference of top 124.

Proximal coupling 104 includes graft material 126 and one or more circumferential stents 128. Graft material 126 includes any one of the graft materials as discussed above in relation to graft material 116. In addition, circumferential stents 128 are similar to or identical to circumferential stents 118 as discussed above.

Further, proximal coupling 104 includes a longitudinal axis LA2. A lumen 130 is defined by graft material 126, and generally by proximal coupling 104. Lumen 130 extends generally parallel to longitudinal axis LA2 and between base 122 and top 124 of proximal coupling 104. Lumen 130 of proximal coupling 104 is in fluid communication with lumen 120 of main body 102.

Distal coupling 106 extends radially from main body 102. Distal coupling 106 corresponds with an opening in main body 102. Distal coupling 106 is generally frustoconically shaped and includes a base 132 and a top 134. A circumference of base 132 is greater than a circumference of top 134.

Distal coupling 106 includes graft material 136 and one or more circumferential stents 138. Graft material 136 includes any one of the graft materials as discussed above in relation to graft material 116. In addition, circumferential stents 138 are similar to or identical to circumferential stents 118 as discussed above.

Further, distal coupling 106 includes a longitudinal axis LA3. A lumen 140 is defined by graft material 136, and generally by distal coupling 106. Lumen 140 extends generally parallel to longitudinal axis LA3 and between base 132 and top 134 of distal coupling 106. Lumen 140 of distal coupling 106 is in fluid communication with lumen 120 of main body 102.

Distal coupling 106 is distal of proximal coupling 104. More particularly, distal coupling 106 is located between distal end 114 of main body 102 and proximal coupling 104. Further, proximal coupling is located between proximal end 110 of main body 102 and distal coupling 106.

In one embodiment, a center to center distance D1 between proximal coupling 104 and distal coupling 106 is set to a predetermined value depending upon the particular branch vessels to be perfused through proximal coupling 104 and distal coupling 106.

In one embodiment, proximal coupling 104 and distal coupling 106 have the same radial orientation, i.e., are radially aligned, on main body 102. For example, in an unbent and straight configuration as illustrated in FIG. 1, longitudinal axis LA2 of proximal coupling 104 is parallel to longitudinal axis LA3 of distal coupling 106. Further, longitudinal axis LA2 of proximal coupling 104 and longitudinal axis LA3 of distal coupling 106 extend radially from and perpendicular to longitudinal axis LA1 of main body 102. This allows proximal coupling 104 and distal coupling 106 to be located on the convex upper surface of the aortic arch when single multibranch stent device 100 is deployed in the aorta as discussed in further detail below. However, in another embodiment, proximal coupling 104 and distal coupling 106 are radially offset, e.g., depending upon the radial orientation of the branch vessels to be perfused by proximal coupling 104 and distal coupling 106, as discussed further below, e.g., in reference to FIGS. 15A, 15B, and/or 15C.

Main body 102, proximal coupling 104 and distal coupling 106 are a single piece, i.e., are separate pieces permanently coupled together or portions of a single piece. For example, a single piece of graft material is cut and sewn to form single multibranch stent device 100, i.e., graft materials 116, 126, 136 are different portions of a single piece of graft material.

Alternatively, graft materials 116, 126, 136 are different materials that are sewn together. For example, main body 102 is formed from a single piece of graft material 116 that is sewn into a tubular shape. Openings are formed in graft material 116 and generally in main body 102. Graft materials 126, 136 of proximal and distal couplings 104, 106 are then sewn, e.g., with stitching, or otherwise coupled, to graft material 116 of main body 102 at the openings.

In either embodiment, single multibranch stent device 100 is a single piece. By forming single multibranch stent device 100 as a single piece, single multibranch stent device 100 can be deployed in a single deployment. This maximizes simplicity of the deployment procedure as compared to deployment of a plurality of separate pieces that are combined together, e.g., using friction from expanded stents, in situ.

Figure 2:
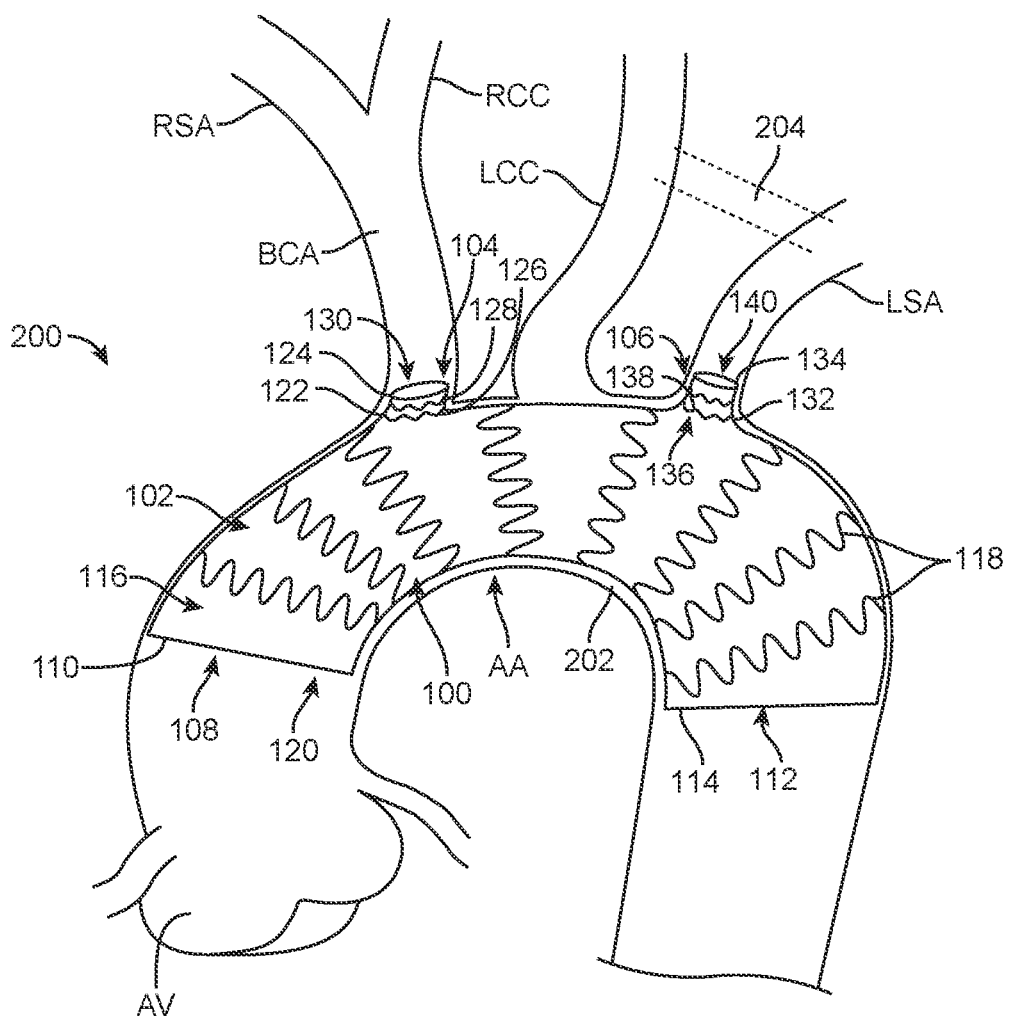
FIG. 2 is a cross-sectional view of a vessel assembly including the single multibranch stent device of FIG. 1 during deployment in accordance with one embodiment.

FIG. 2 is a cross-sectional view of a vessel assembly 200 including single multibranch stent device 100 of FIG. 1 during deployment in accordance with one embodiment. Referring to FIGS. 1 and 2 together, the thoracic aorta 202 has numerous arterial branches. The arch AA of the aorta 202 has three major branches extending therefrom, all of which usually arise from the convex upper surface of the arch AA. The brachiocephalic artery BCA originates anterior to the trachea. The brachiocephalic artery BCA divides into two branches, the right subclavian artery RSA (which supplies blood to the right arm) and the right common carotid artery RCC (which supplies blood to the right side of the head and neck).

The left common carotid artery LCC arises from the arch AA of the aorta 202 just to the left of the origin of the brachiocephalic artery BCA. The left common carotid artery LCC supplies blood to the left side of the head and neck. The third branch arising from the aortic arch AA, the left subclavian artery LSA, originates behind and just to the left of the origin of the left common carotid artery LCC and supplies blood to the left arm. The left subclavian artery LSA and the left common carotid artery LCC are distal to the brachiocephalic artery BCA and are sometimes called aortic branch arteries distal of the brachiocephalic artery BCA.

However, a significant proportion of the population has only two great branch vessels coming off the aortic arch AA while others have four great branch vessels coming of the aortic arch AA. Accordingly, although a particular anatomical geometry of the aortic arch AA is illustrated and discussed, in light of this disclosure, those of skill in the art will understand that the geometry of the aortic arch AA has anatomical variations and that the various structures as disclosed herein would be modified accordingly.

Aneurysms, dissections, penetrating ulcers, intramural hematomas and/or transections, generally referred to as a diseased region of the aorta 202, may occur in the aorta arch AA and the peripheral arteries BCA, LCC, LSA. For example, thoracic aortic aneurysms include aneurysms present in the ascending thoracic aorta, the aortic arch AA, and one or more of the branch arteries BCA, LCC, LSA that emanate therefrom. Thoracic aortic aneurysms also include aneurysms present in the descending thoracic aorta and branch arteries that emanate therefrom. Accordingly, the aorta 202 as illustrated in FIG. 2 has a diseased region similar to any one of those discussed above which will be bypassed and excluded using single multibranch stent device 100 as discussed below.

As illustrated in FIG. 2, single multibranch stent device 100 is deployed into aorta 202, e.g., via femoral access. For example, to deploy single multibranch stent device 100, a guide wire is introduced via femoral access, i.e., is inserted into the femoral artery and routed up through the abdominal aorta, and into the thoracic aorta.

A delivery system including single multibranch stent device 100 is introduced via femoral access and is advanced into the ascending aorta 202 over the guidewire. The delivery system is positioned at the desired location such that the position of single multibranch stent device 100 is in the ascending aorta near the aortic valve AV. Single multibranch stent device 100 is then deployed from the delivery system, e.g., by removal of a sheath constraining single multibranch stent device 100. By forming single multibranch stent device 100 as a single piece, single multibranch stent device 100 is deployed in a single operation maximizing simplicity and minimizing the procedure time.

In accordance with this embodiment, single multibranch stent device 100 is deployed such that proximal coupling 104 is aligned with the brachiocephalic artery BCA and distal coupling 106 is aligned with the left subclavian artery LSA. Main body 102 is located and fixed within aorta 202 such that proximal opening 108 is proximal of the brachiocephalic artery BCA and distal opening 112 is distal of the left subclavian artery LSA.

Accordingly, blood flow enters proximal opening 108 of main body 102, flows through lumen 120 of main body 102, and exits distal opening 112 of main body 102 and into the aorta 202.

Further, blood flow from lumen 120 of main body 102 flows through lumen 130 of proximal coupling 104 and into the brachiocephalic artery BCA. More particularly, blood flows enter into base 122 of proximal coupling 104, through lumen 130 of proximal coupling 104, and exits top 124 of proximal coupling 104 into the brachiocephalic artery BCA.

In addition, blood flow from lumen 120 of main body 102 flows through lumen 140 of distal coupling 106 and into the left subclavian artery LSA. More particularly, blood flows enter into base 132 of distal coupling 106, through lumen 140 of distal coupling 106, and exits top 134 of distal coupling 106 into the left subclavian artery LSA.

Upon completion of deployment of single multibranch stent device 100, blood flows through main body 102, proximal coupling 104, and distal coupling 106 thus perfusing the distal territories. At the same time, single multibranch stent device 100 excludes any overlapped diseased regions of the aorta 202.

In accordance with this embodiment, single multibranch stent device 100, and more particularly, main body 102, overlaps, excludes and thus occludes the left common carotid artery LCC. In accordance with this embodiment, a bypass 204 provides perfusion to the left common carotid artery LCC. Illustratively, bypass 204 provides perfusion of the left common carotid artery LCC from the left subclavian artery LSA.

Bypass 204 is surgically inserted during the same procedure as deployment of single multibranch stent device 100. However, in another embodiment, bypass 204 is surgically inserted prior to deployment of single multibranch stent device 100, e.g., to simplify the procedure.

Figure 3:
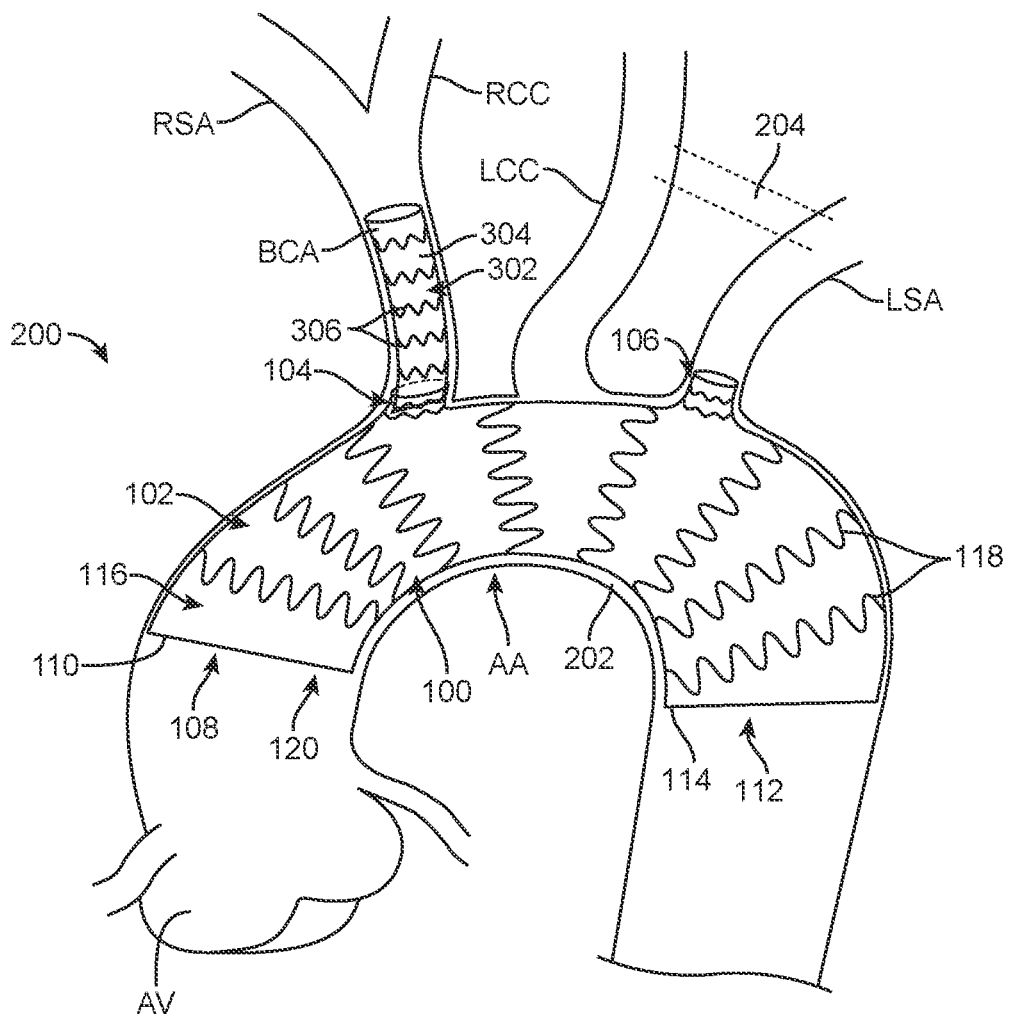
FIG. 3 is a cross-sectional view of the vessel assembly of FIG. 2 at a later stage during deployment of a first bridging stent graft in accordance with one embodiment.

FIG. 3 is a cross-sectional view of vessel assembly 200 of FIG. 2 at a later stage during deployment of a first bridging stent graft 302, sometimes called a bridging stent or proximal bridging stent graft 302, in accordance with one embodiment. Referring now to FIG. 3, bridging stent graft 302 is located within proximal coupling 104 and the brachiocephalic artery BCA. More particularly, bridging stent graft 302 self-expands (or is balloon expanded) to be anchored within proximal coupling 104 and the brachiocephalic artery BCA.

Bridging stent graft 302 includes graft material 304 and one or more circumferential stents 306. Graft material 304 includes any one of the graft materials as discussed above in relation to graft material 116. In addition, circumferential stents 306 are similar to or identical to circumferential stents 118 as discussed above.

Upon deployment of bridging stent graft 302, blood flow into proximal coupling 104 is bridged and passed into the brachiocephalic artery BCA through bridging stent graft 302.

In one embodiment, bridging stent graft 302 is deployed via femoral access. For example, to deploy bridging stent graft 302, a guide wire is introduced via femoral access, i.e., is inserted into the femoral artery and routed up and into distal opening 112 of main body 102. The guidewire is then routed through proximal coupling 104 and into the brachiocephalic artery BCA.

A delivery system including bridging stent graft 302 is introduced via femoral access and is advanced into proximal coupling 104 and the brachiocephalic artery BCA over the guidewire. Bridging stent graft 302 is then deployed from the delivery system, e.g., by removal of a sheath constraining bridging stent graft 302.

In another embodiment, bridging stent graft 302 is deployed via supra aortic access. For example, to deploy bridging stent graft 302, a guide wire is introduced through the right subclavian artery RSA, and advanced into main body 102 through proximal coupling 104.

A delivery system including bridging stent graft 302 is introduced via supra aortic access and is advanced into the brachiocephalic artery BCA and proximal coupling 104 over the guidewire. Bridging stent graft 302 is then deployed from the delivery system, e.g., by removal of a sheath constraining bridging stent graft 302.

Figure 4:
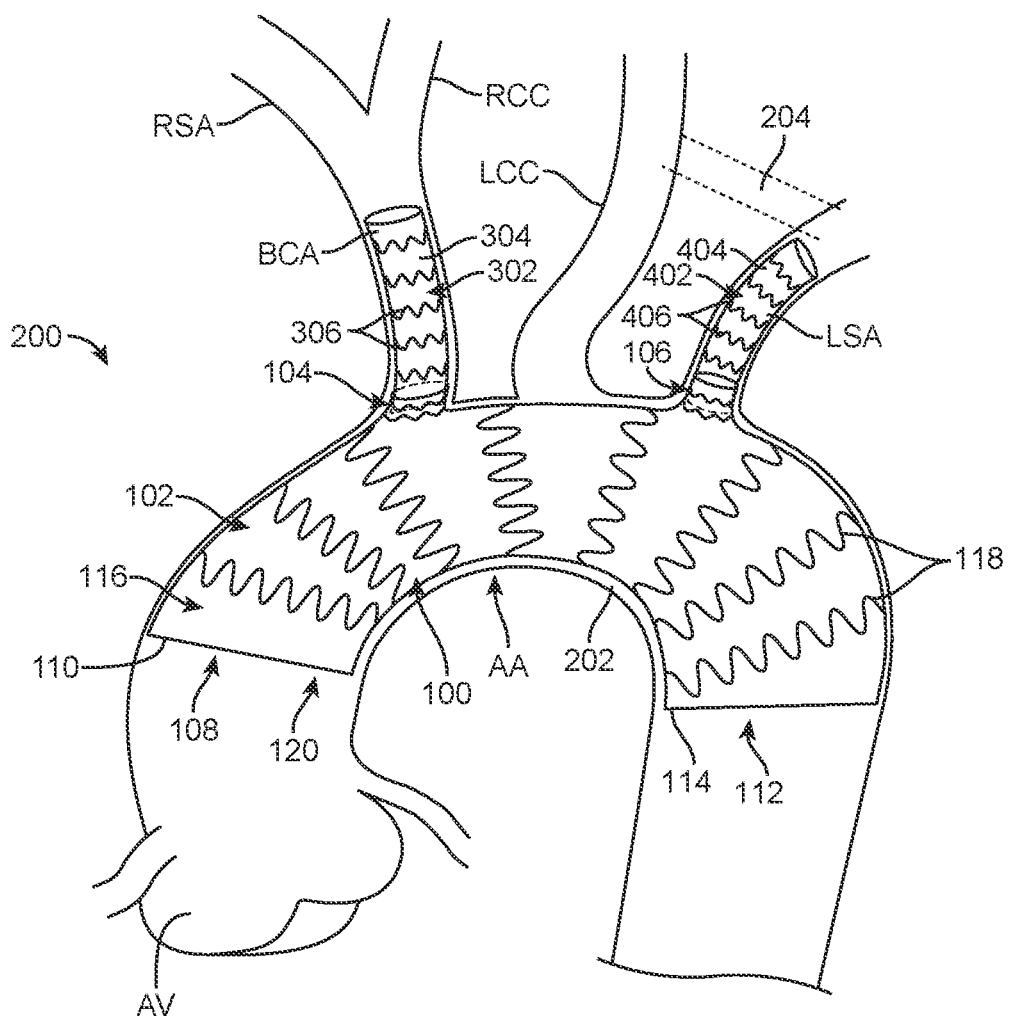
FIG. 4 is a cross-sectional view of the vessel assembly of FIG. 3 at a later stage during deployment of a second bridging stent graft in accordance with one embodiment.

FIG. 4 is a cross-sectional view of vessel assembly 200 of FIG. 3 at a later stage during deployment of a second bridging stent graft 402, sometimes called a bridging stent or distal bridging stent graft 402, in accordance with one embodiment. Referring now to FIG. 4, bridging stent graft 402 is deployed within distal coupling 106 and the left subclavian artery LSA. More particularly, bridging stent graft 402 self-expands (or is balloon expanded) to be anchored within distal coupling 106 and the left subclavian artery LSA.

Bridging stent graft 402 includes graft material 404 and one or more circumferential stents 406. Graft material 404 includes any one of the graft materials as discussed above in relation to graft material 116. In addition, circumferential stents 406 are similar to or identical to circumferential stents 118 as discussed above.

Upon deployment of bridging stent graft 402, blood flow into distal coupling 106 is bridged and passed into the left subclavian artery LSA through bridging stent graft 402.

In one embodiment, bridging stent graft 402 is deployed via femoral access. For example, to deploy bridging stent graft 402, a guide wire is introduced via femoral access, i.e., is inserted into the femoral artery and routed up and into distal opening 112 of main body 102. The guidewire is then routed through distal coupling 106 and into the left subclavian artery LSA.

A delivery system including bridging stent graft 402 is introduced via femoral access and is advanced into distal coupling 106 and the left subclavian artery LSA over the guidewire. Bridging stent graft 402 is then deployed from the delivery system, e.g., by removal of a sheath constraining bridging stent graft 402.

In another embodiment, bridging stent graft 402 is deployed via supra aortic access. For example, to deploy bridging stent graft 402, a guide wire is introduced through the left subclavian artery LSA, and advanced into main body 102 through distal coupling 106.

A delivery system including bridging stent graft 402 is introduced via supra aortic access and is advanced into the left subclavian artery LSA and distal coupling 106 over the guidewire. Bridging stent graft 402 is then deployed from the delivery system, e.g., by removal of a sheath constraining bridging stent graft 402.

Although deployment of bridging stent graft 302 is described above as occurring before deployment of bridging stent graft 402, in other embodiments, bridging stent graft 402 is deployed prior to deployment of bridging stent graft 302.

Figure 5:
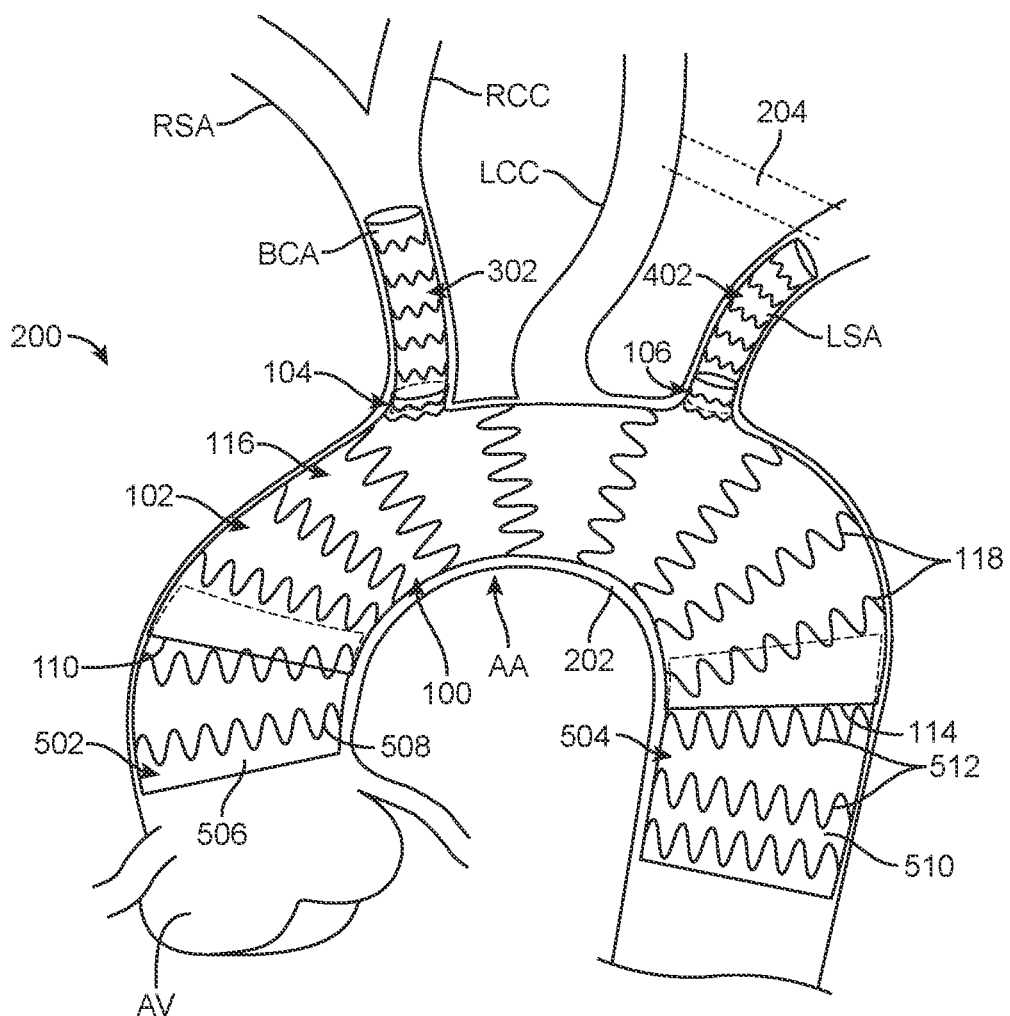
FIG. 5 is a cross-sectional view of the vessel assembly of FIG. 4 at a later stage during deployment of a proximal extension and a distal extension in accordance with one embodiment.

FIG. 5 is a cross-sectional view of vessel assembly 200 of FIG. 4 at a later stage during deployment of a proximal extension 502 and a distal extension 504 in accordance with one embodiment. Referring now to FIG. 5, optionally, proximal extension 502, sometime called a proximal cuff 502 or tubular structure, is coupled to main body 102 and extend proximately therefrom. For example, proximal cuff 502 is deployed in the event that proximal end 110 of main body 102 is deployed distally from the aortic valve AV to extend between the desired deployment location and proximal end 110 of main body 102. Proximal extension 502 is optional and in one embodiment is not deployed or used.

Proximal extension 502 includes graft material 506 and one or more circumferential stents 508. Graft material 506 includes any one of the graft materials as discussed above in relation to graft material 116. In addition, circumferential stents 508 are similar to or identical to circumferential stents 118 as discussed above.

In addition, and optionally, distal extension 504 is coupled to main body 102 and extend distally therefrom. For example, distal extension 504 is added using a thoracic device and can take any one of a number of forms depending upon the condition being treated. Distal extension 504 is optional and in one embodiment is not deployed or used.

Distal extension 504 includes graft material 510 and one or more circumferential stents 512. Graft material 510 includes any one of the graft materials as discussed above in relation to graft material 116. In addition, circumferential stents 512 are similar to or identical to circumferential stents 118 as discussed above.

Figure 6:
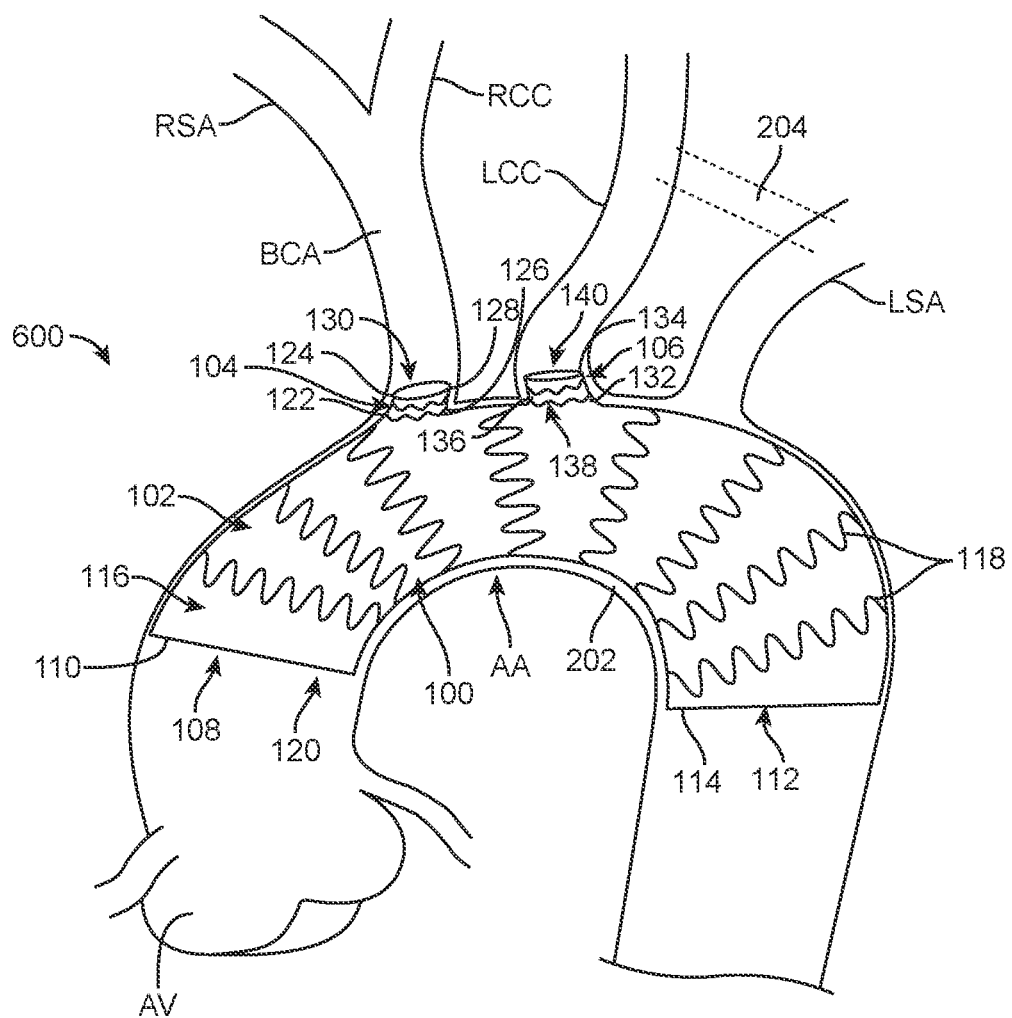
FIG. 6 is a cross-sectional view of a vessel assembly including the single multibranch stent device of FIG. 1 during deployment in accordance with another embodiment.

FIG. 6 is a cross-sectional view of a vessel assembly 600 including single multibranch stent device 100 of FIG. 1 during deployment in accordance with another embodiment. Vessel assembly 600 of FIG. 6 is similar to vessel assembly 200 of FIG. 2 and only the significant differences are discussed below.

Referring now to FIGS. 1 and 6 together, in accordance with this embodiment, single multibranch stent device 100 is deployed such that proximal coupling 104 is aligned with the brachiocephalic artery BCA and distal coupling 106 is aligned with the left common carotid artery LCC. Illustratively distance D1 between proximal coupling 104 and distal coupling 106 in the embodiment of FIG. 6 is less than distance D1 in embodiment of FIG. 2. Main body 102 is located and fixed within aorta 202 such that proximal opening 108 is proximal of the brachiocephalic artery BCA and distal opening 112 is distal of the left subclavian artery LSA.

Accordingly, blood flow from lumen 120 of main body 102 flows through lumen 140 of distal coupling 106 and into the left common carotid artery LCC. More particularly, blood flows enter into base 132 of distal coupling 106, through lumen 140 of distal coupling 106, and exits top 134 of distal coupling 106 into the left common carotid artery LCC.

In accordance with this embodiment, single multibranch stent device 100, and more particularly, main body 102, overlaps, excludes and thus occludes the left subclavian artery LSA. In accordance with this embodiment, bypass 204 provides perfusion to the left subclavian artery LSA. Illustratively, bypass 204 provides perfusion of the left subclavian artery LSA from the left common carotid artery LCC.

Figure 7:
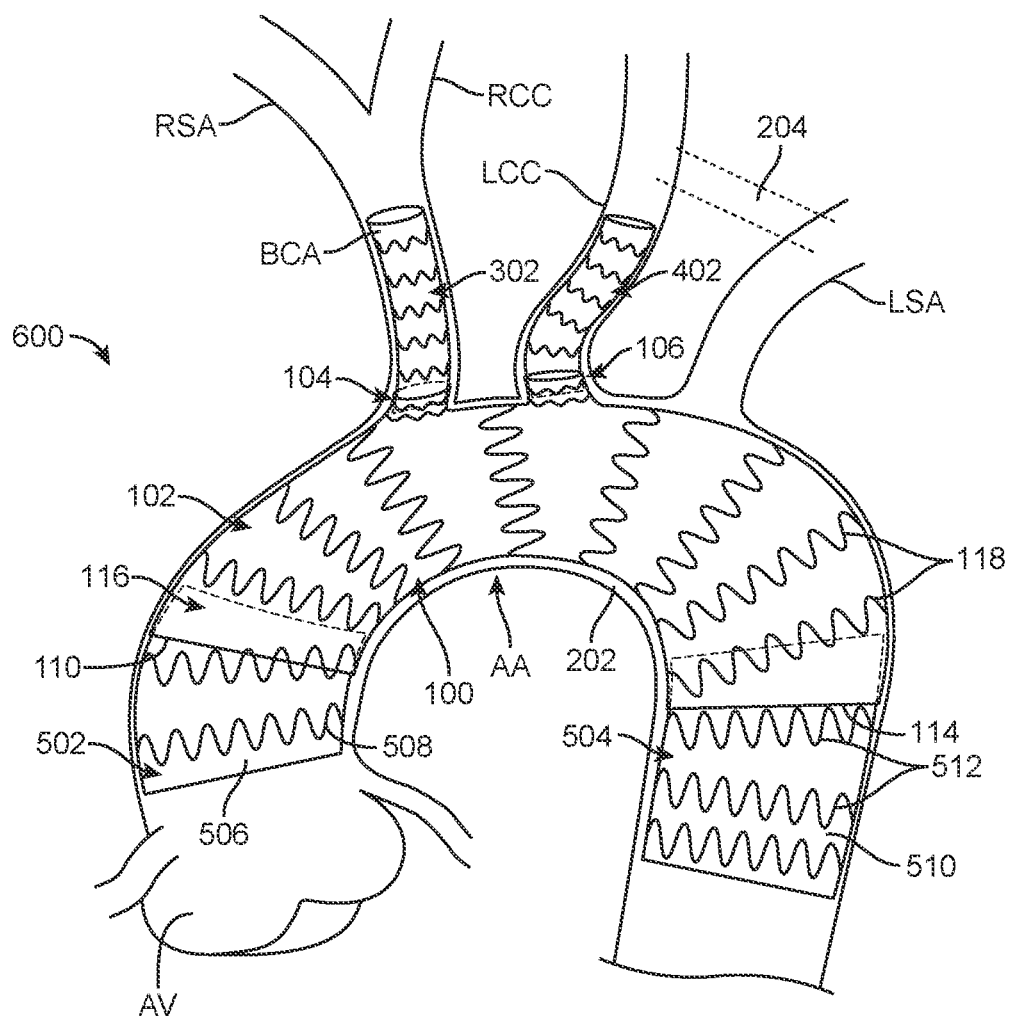
FIG. 7 is a cross-sectional view of the vessel assembly of FIG. 6 at a later stage during deployment of the first bridging stent graft and the second bridging stent graft.

FIG. 7 is a cross-sectional view of vessel assembly 600 of FIG. 6 at a later stage during deployment of first bridging stent graft 302 and second bridging stent graft 402. Deployment of first bridging stent graft 302 in the view of FIG. 6 is similar or identical to deployment of first bridging stent graft 302 in the view of FIG. 3 as discussed above and so the description is not repeated for simplicity.

In accordance with this embodiment, bridging stent graft 402 is deployed within distal coupling 106 and the left common carotid artery LCC. More particularly, bridging stent graft 402 self-expands (or is balloon expanded) to be anchored within distal coupling 106 and the left common carotid artery LCC.

Upon deployment of bridging stent graft 402, blood flow into distal coupling 106 is bridged and passed into the left common carotid artery LCC through bridging stent graft 402.

In one embodiment, bridging stent graft 402 is deployed via femoral access. For example, to deploy bridging stent graft 402, a guide wire is introduced via femoral access, i.e., is inserted into the femoral artery and routed up and into distal opening 112 of main body 102. The guidewire is then routed through distal coupling 106 and into the left common carotid artery LCC.

A delivery system including bridging stent graft 402 is introduced via femoral access and is advanced into distal coupling 106 and the left common carotid artery LCC over the guidewire. Bridging stent graft 402 is then deployed from the delivery system, e.g., by removal of a sheath constraining bridging stent graft 402.

In another embodiment, bridging stent graft 402 is deployed via supra aortic access. For example, to deploy bridging stent graft 402, a guide wire is introduced through the left common carotid artery LCC, and advanced into main body 102 through distal coupling 106.

A delivery system including bridging stent graft 402 is introduced via supra aortic access and is advanced into the left common carotid artery LCC and distal coupling 106 over the guidewire. Bridging stent graft 402 is then deployed from the delivery system, e.g., by removal of a sheath constraining bridging stent graft 402.

Optionally, proximal extension 502 and/or distal extension 504 are coupled to main body 102 as described above.

In the embodiments described above, proximal coupling 104 is aligned with the brachiocephalic artery BCA and distal coupling 106 is aligned with either the left subclavian artery LSA (FIG. 5) or the left common carotid artery LCC (FIG. 7). As used herein, a coupling is aligned with a respective artery when the longitudinal axis, e.g., longitudinal axis LA2 or LA3, are parallel to and point into the respective artery. In other words, a coupling is aligned with a respective artery when the coupling is located within the ostia of the respective artery.

However, in certain instances, a coupling is offset, sometimes called misplaced or misaligned, with the respective artery, e.g., due to physician deployment inaccuracy. In these instances, the coupling points into the wall of aorta 202 and there is a longitudinal distance between the coupling and the respective artery.

Figure 8:
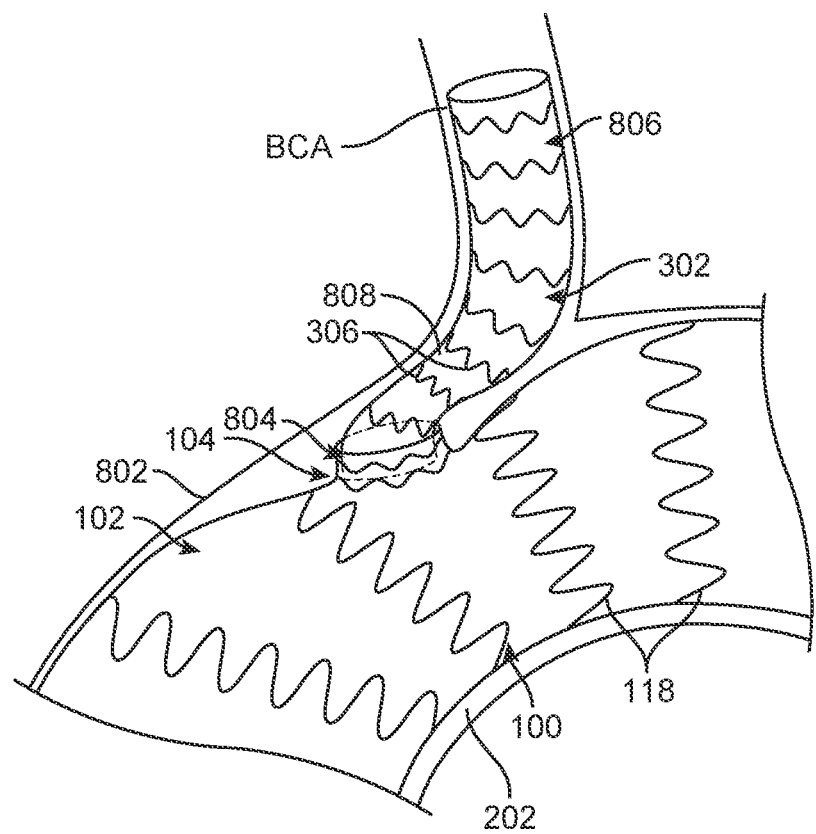
FIG. 8 is a perspective view of a proximal coupling of the single multibranch stent device of the vessel assembly of FIG. 5 or the vessel assembly of FIG. 7 misaligned with the brachiocephalic artery in accordance with one embodiment.

FIG. 8 is a perspective view of proximal coupling 104 of single multibranch stent device 100 of vessel assembly 200 of FIG. 5 or vessel assembly 600 of FIG. 7 misaligned with the brachiocephalic artery BCA in accordance with one embodiment. In accordance with this embodiment, proximal coupling 104 is offset from the brachiocephalic artery BCA. Illustratively, proximal coupling 104 is located proximally to the brachiocephalic artery BCA, i.e., the ostium thereof, although in another embodiment, proximal coupling 104 is located distally to the brachiocephalic artery BCA. In either embodiment, proximal coupling 104 points into the wall 802 of aorta 202.

In accordance with this embodiment, bridging stent graft 302 bridges the displacement between proximal coupling 104 and the brachiocephalic artery BCA. In other words, a proximal end 804 of bridging stent graft 302 is coupled to proximal coupling 104 and a distal end 806 of bridging stent graft 302 is coupled to the brachiocephalic artery BCA. A main body 808 of bridging stent graft 302 extends between, e.g., parallel to, main body 102 of single multibranch stent device 100 and wall 802 of aorta 202.

To avoid collapse of bridging stent graft 302 between main body 102 and wall 802, bridging stent graft 302 is configured to exert a higher radial force than the radial force of main body 102. As used herein, "radial force" includes both a radial force exerted during expansion/deployment as well as a chronic radial force continuously exerted after implantation such that a scaffold has a predetermined compliance or resistance as the surrounding native anatomy, e.g., aorta 202, expands and contracts during the cardiac cycle. The radial force of main body 102 is configured to be lower than that of bridging stent graft 302 to avoid collapse of bridging stent graft 302 when main body 102 is deployed against and adjacent thereof and thus maintains perfusion of the brachiocephalic artery BCA as discussed above. If there is any collapse, the collapse is a partial collapse in main body 102 by bridging stent graft 302.

To configure bridging stent graft 302 and main body 102 with differing relative radial forces, circumferential stents 306 of bridging stent graft 302 are constructed with relatively thicker and/or shorter segments of material than circumferential stents 118 of main body 102. Shorter and/or thicker circumferential stents 306 have less flexibility but greater radial force to ensure that circumferential stents 118 of main body 102 do not collapse the lumen of bridging stent graft 302. Other variations or modification of circumferential stents 306, 118 may be used to achieve relative radial forces in other embodiments.

Although displacement of proximal coupling 104 and the brachiocephalic artery BCA is discussed above, the discussion is equally applicable to displacement of distal coupling 106 and either the left subclavian artery LSA (FIG. 5) or the left common carotid artery LCC (FIG. 7). In the event that distal coupling 106 is displaced, either proximally or distally, with either the left subclavian artery LSA (FIG. 5) or the left common carotid artery LCC (FIG. 7), bridging stent graft 402 bridges the displacement. Bridging stent graft 402 is configured to exert a higher radial force than the radial force of main body 102 to avoid collapse in a manner similar to that discussed above regarding bridging stent graft 302. Generally, in FIG. 8, proximal coupling 104 is also representative of distal coupling 106, the brachiocephalic artery BCA is also representative of either the left subclavian artery LSA (FIG. 5) or the left common carotid artery LCC (FIG. 7), and bridging stent graft 302 is also representative of bridging stent graft 402.

In one embodiment, both proximal coupling 104 and distal coupling 106 are offset from their respective arteries BCA and LSA/LCC. In other embodiments, only proximal coupling 104 or distal coupling 106 are offset from their respective arteries BCA and LSA/LCC. In yet another embodiment, proximal coupling 104 and distal coupling 106 are both aligned with their respective arteries BCA and LSA/LCC.

With reference to FIGS. 9 to 14, example embodiments are shown of deployment mechanisms and methods that may be used with any of the stent devices or device assemblies disclosed herein (e.g., as shown in FIGS. 1-8). In one embodiment, there may be a primary or main guidewire (GW1) and an additional guidewire for each coupling/volcano/MEC on the stent device. For example, if the stent device has two couplings, three guidewires may be used—the primary guidewire (GW1), a second guidewire (GW2), and a third guidewire (GW3). The guidewires that are associated with the couplings may be "through and through" guidewires, in that they enter the body at one location and exit the body at another location. For example, in the embodiment shown, guidewire GW2 may extend from a femoral access site (or other site in the leg), through the aorta, into the artery BCA, and exit from the patient's right arm, torso, or neck (or vice versa). Similarly, guidewire GW3 may extend from a femoral access site (or other site in the leg), through the aorta, into the artery LSA, and exit from the patient's left arm or torso (or vice versa). Of course, the guidewires may extend through any combination of the great vessels in the arch and the naming conventions are merely for ease of illustration. The primary guidewire GW1 may be a standard guidewire that extends into the ascending aorta and is used to guide the tapered tip 902 of the stent device.

Figure 9:
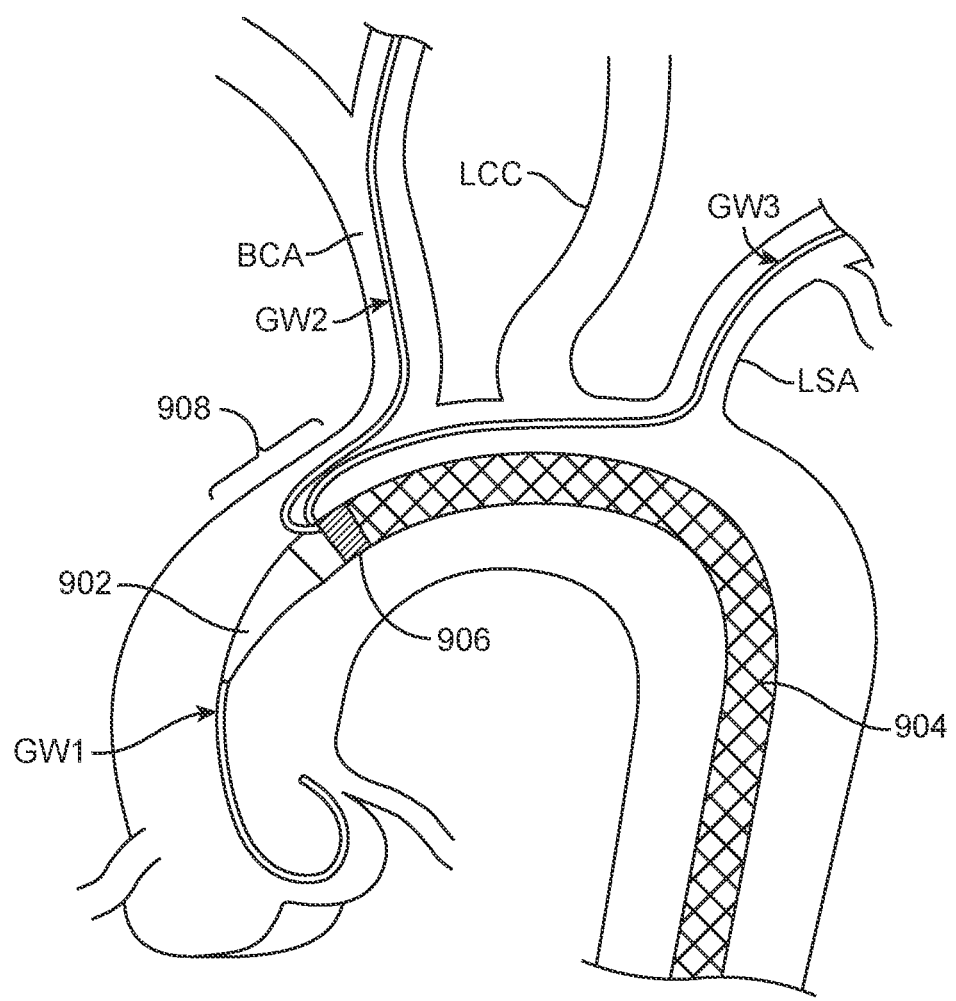
FIGS. 9, 10, 11, 12, 13, 14, 15A, 15B, and 15C are example embodiments of deployment mechanisms and methods that may be used with any of the stent devices or device assemblies as disclosed herein.

With particular reference to FIG. 9, an example is shown of a device being deployed that has two couplings that are pre-wired with guidewires GW2 and GW3. As described above, guidewire GW1 may be a standard guidewire used to guide the device to the target location in the aorta. In the embodiment shown, guidewire GW2 is pre-wired through a coupling configured to be deployed in, at, or near the artery BCA ostium and guidewire GW3 is pre-wired through a coupling configured to be deployed in, at, or near the artery LSA ostium. As described above, guidewires GW2 and GW3 may be through and through guidewires that are inserted prior to device deployment. The catheter including the stent device may be loaded onto all three guidewires (described in more detail, below, with reference to FIGS. 13-14) and inserted into the patient at the femoral access site. The catheter may be navigated to the aortic arch, as shown in FIG. 9, for deployment of the stent device to begin.

As shown in FIG. 9, guidewires GW2 and GW3 may exit the catheter at or adjacent to a proximal end of the tapered tip 902. Guidewires GW2 and GW3 extend between the constraining sheath 904 and an outer surface of the stent device until they reach their corresponding coupling. As illustrated, there is a radiopaque marker 906 and a guidewire exit area 908 for guidewires GW2 and GW3. When the guidewires reach their coupling, they extend through the coupling and into the interior of the stent device. The guidewires then extend through the interior of the stent device and out through the catheter to the femoral access site. In the example shown, guidewire GW2 extends through the coupling intended for the artery BCA and guidewire GW3 extends through the coupling intended for the artery LSA. However, there may be couplings intended for any combination of the three great vessels, and guidewires may extend through any or all of them in other embodiments.

Figure 10:
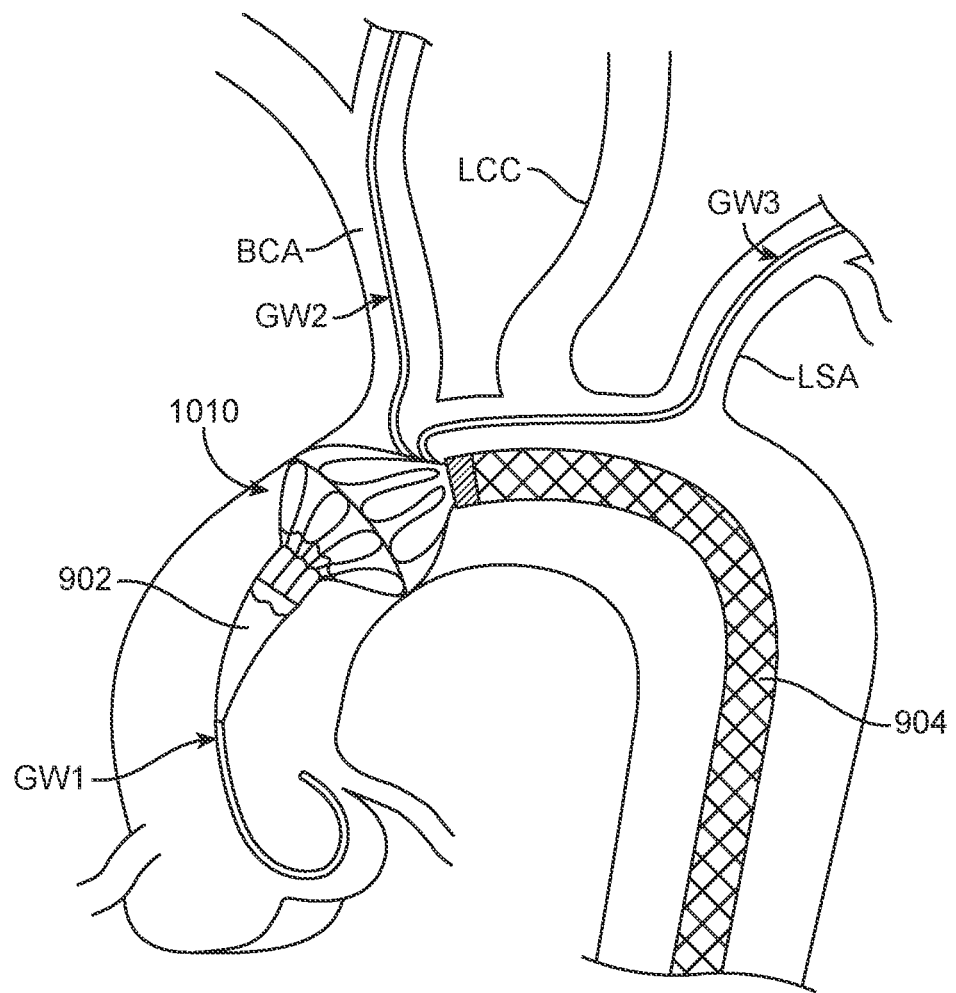

With reference to FIG. 10, the stent device may begin deployment by retracting the constraining sheath 904 to begin to expose the first rows of stent rings. In the example shown, the delivery system includes a tip capture mechanism 1010 to retain the first row of stent rings in a constrained state until some or all of the stent device has been deployed. As the constraining sheath is retracted, portions of the guidewires GW2 and GW3 that were trapped between the sheath and the stent device are freed.

Figure 11:
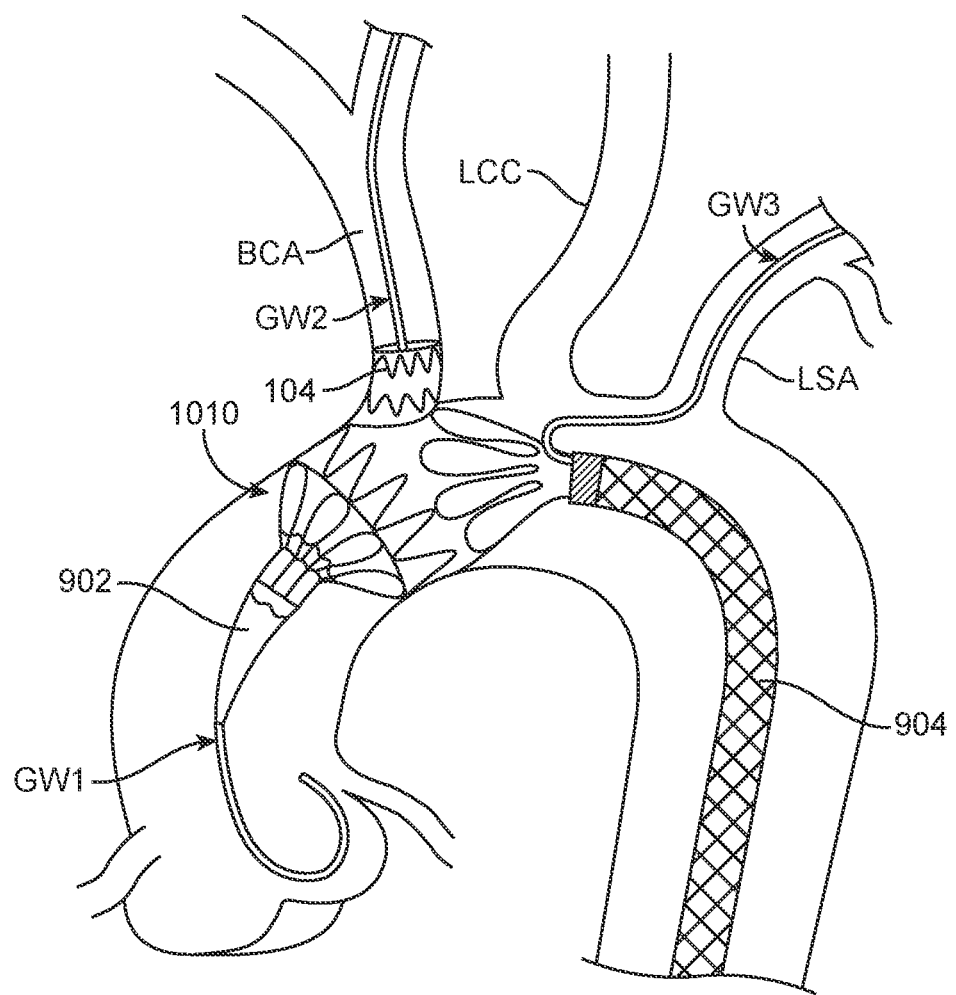

With reference to FIG. 11, as the constraining sheath 904 continues to be retracted, the first coupling 104 is released. Due to the pre-wiring of guidewire GW2 through the coupling 104 and the artery BCA, the coupling 104 is deployed within the artery BCA ostium, or very near to it, and is already cannulated by the guidewire GW2. If the coupling 104 is not completely aligned with the artery BCA ostium, the physician(s) may use the through and through guidewire GW2 to manipulate the coupling 104 by applying tension to the guidewire GW2 and applying force to one or both exposed/exterior portions of the guidewire GW2 to adjust the coupling 104 to a more well-aligned position. This may be done at the current stage or when more or all of the stent device has been deployed.

Figure 12:
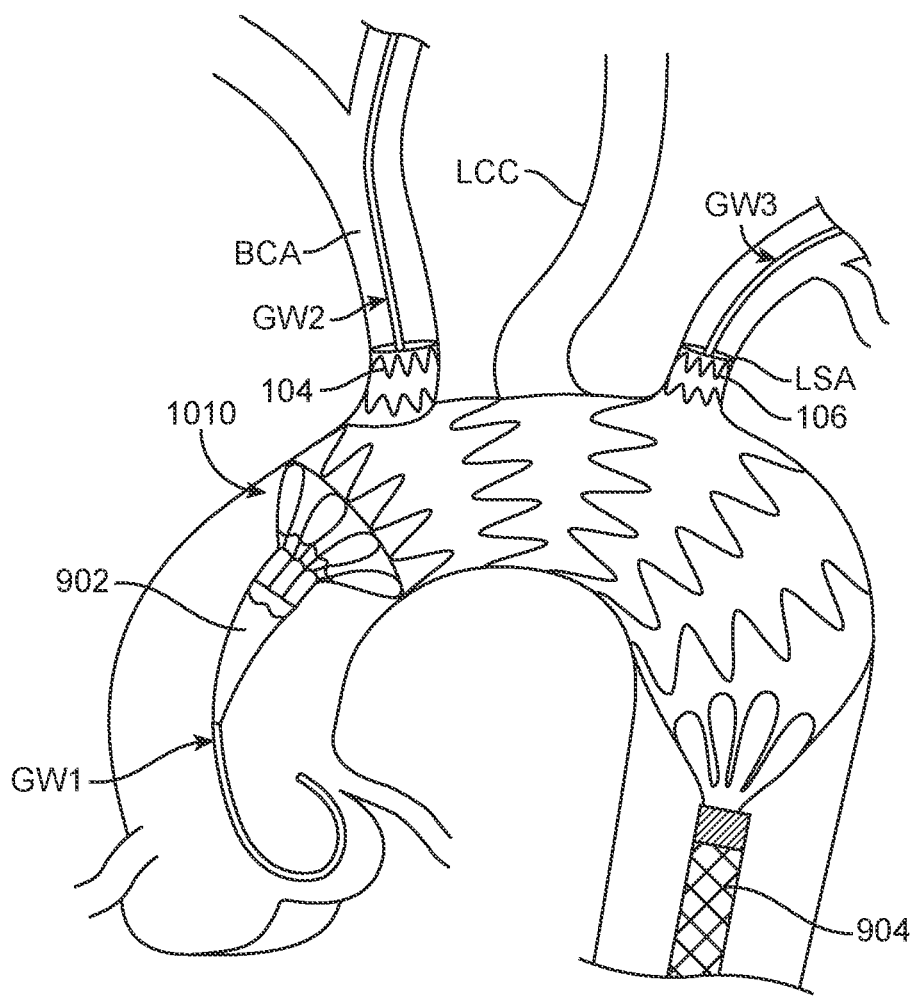

With reference to FIG. 12, the constraining sheath 904 is further retracted such that the second coupling 106 is released. Similar to the first coupling 104, the pre-wiring of guidewire GW3 causes the second coupling 106 to be deployed within the artery LSA ostium, or very near to it, and already cannulated by the guidewire GW3. As with the first coupling 104, the physician(s) may manipulate the second coupling 106 using the guidewire GW3 to improve the alignment of the coupling 106 with the artery LSA. Once the second coupling 106 has been released, the physician may continue to retract the constraining sheath 904 until the entire stent device is deployed. Once the device has been positioned to the physician's liking, the tip capture mechanism 1010 may be activated to release the proximal stents to anchor the stent device in place.

Following deployment of the stent device, bridging stent grafts may be deployed within the couplings 104, 106, as shown in FIGS. 3-8. Deployment of the bridging stent grafts may be made significantly easier and more accurate due to the pre-wired couplings. As shown in FIG. 12, both couplings 104, 106 are already cannulated by the guidewires GW2 and GW3, therefore, the bridging stent grafts may be easily navigated to the couplings 104, 106 and deployed therein. Unlike with a non-pre-wired deployment, there is no risk that the physician will not be able to locate the opening in the coupling. This is especially significant if the coupling is not located within or near the ostium. This may occur, for example, if the dimensions or orientation of the couplings do not closely match the anatomy of the patient. In this case, while the first coupling may be well-aligned with the first ostium (e.g., artery BCA), the second coupling may be located axially proximal or distal to the target ostium and/or it may be rotated circumferentially relative to the target ostium. In this situation, it may be very difficult for the physician to access the opening in the coupling using conventional methods. However, when the couplings are pre-wired with the guidewire, the physician merely has to advance the bridging stent graft over the guidewire and it will automatically find the coupling opening by virtue of the pre-wiring.

Figure 13:
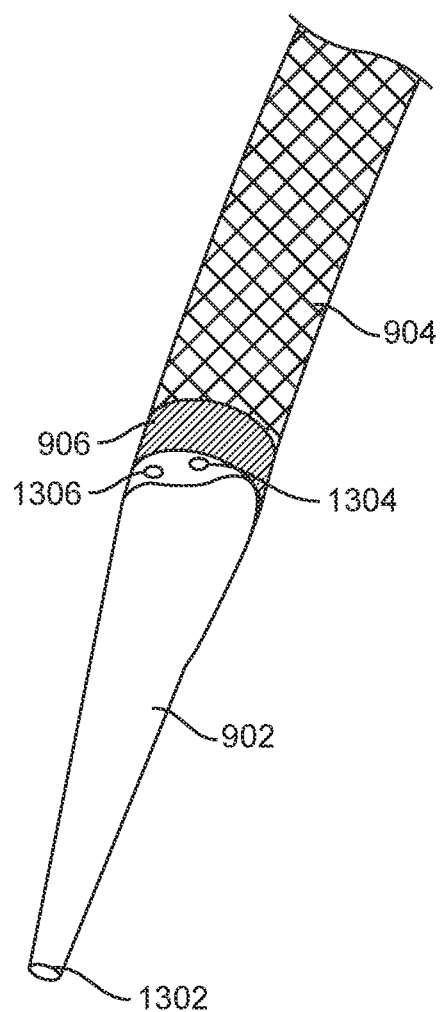
Figure 14:
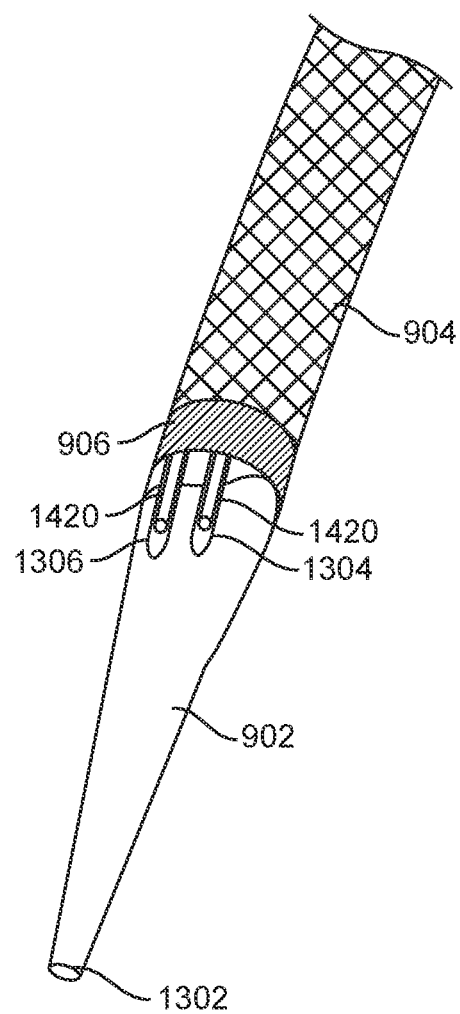

With reference to FIGS. 13 and 14, example embodiments are shown of the distal end of the delivery catheter. In the embodiment shown in FIG. 13, the tapered tip 902 may include a lumen 1302 that extends to the distal tip and which is configured to receive the main/primary guidewire GW1. There may be separate lumens for the through and through guidewires GW2 and GW3, which may be more proximal than the lumen for GW1. In this example, the lumens may be formed at the base or proximal end of the tapered tip. There may be a second lumen 1304 configured to receive guidewire GW2 and a third lumen 1306 configured to receive guidewire GW3. The lumens 1304, 1306 may allow the guidewires GW2, GW3 to pass through the tip 902 and to travel between the constraining sheath 904 and the stent device until they reach their associated coupling, at which point they extend through the coupling and into the interior of the device.

With reference to FIG. 14, in one embodiment, the lumens 1304, 1306 configured to receive guidewires GW2 and GW3 may be formed as grooves in the base of the tapered tip 902. Accordingly, when the constraining sheath 904 is retracted, the guidewires GW2, GW3 may be freed from the tapered tip 902. This may allow the guidewires GW2, GW3 to become aligned in their target vessel and allow the couplings to extend into the target vessel once the sheath is retracted a sufficient length to release them (e.g., as shown in FIGS. 10-12). The grooves 1304, 1306 may be disposed circumferentially spaced about the tapered tip 902 in any configuration. In one example, the two grooves 1304, 1306 may be directly adjacent to each other, such as shown in FIGS. 13 and 14. However, in other embodiments, they may be spaced farther apart, such as on opposite sides of the tip (e.g., 180 degree spacing). In other embodiments, there may be more than two lumens/grooves than there are guidewires. For example, if there are two through and through guidewires, there may be three, four, or more lumens or grooves. In such embodiments, the lumens/grooves may be located directly adjacent to each other or may be spaced apart (e.g., evenly circumferentially spaced). This may give the physician options for which lumen to select for each guidewire and/or provide redundancy. While one example configuration is shown where the lumens are formed as grooves, other configurations may also allow the guidewires to become freed as the sheath is retracted. In the example shown in FIG. 14, there may be a guide lumen 1420 provided for each guidewire. The guide lumen 1420 may be a separate tube or conduit that is configured to receive the guidewire and guide it through the catheter and into the stent device. The guide lumen 1420 may protect the device during guidewire insertion and may provide a lubricious surface to allow the catheter to be loaded onto the guidewire, among other functions.

In at least one embodiment, the axial region of the stent device between two couplings may be more circumferentially flexible (e.g., easier to rotate) than regions axially outside of the couplings. As shown in FIGS. 1-7 and 12, the stent device may have one or more stent rings disposed axially between the two couplings. In one embodiment, there may be exactly one stent ring between the two couplings. In another embodiment, there may be exactly two stent rings between the two couplings. In another embodiment, however, there may be zero stent rings between the two couplings, e.g., the stent device may include only graft material between the two couplings. Having few or no stent rings between the two couplings may increase the circumferential flexibility of the stent device, which may allow it to be rotated during deployment to better align the couplings with the great vessels (e.g., by applying force to the guidewires, as disclosed above, or by rotating the catheter to apply torque, or other techniques, or a combination thereof).

In another embodiment, which may be in combination with the above or independent, the graft material itself may provide increased flexibility in the region between the couplings. In one example, the orientation of the graft material fibers may be different in the region between the couplings compared to other regions or the remainder of the graft. In one embodiment, graft material in the region between the couplings may have fiber orientations that are oblique to the longitudinal axis of the stent device, e.g., not parallel or perpendicular. For example, the fibers may be oriented from 30 to 60 degrees in either direction from parallel. In one embodiment, the fibers may be oriented at 45 degrees in either direction from parallel (e.g., ±45 degrees). The other regions of the graft may have fibers that are oriented parallel and perpendicular to the longitudinal axis. In one embodiment, the fibers may be woven in a plain weave pattern.

Figure 15A:
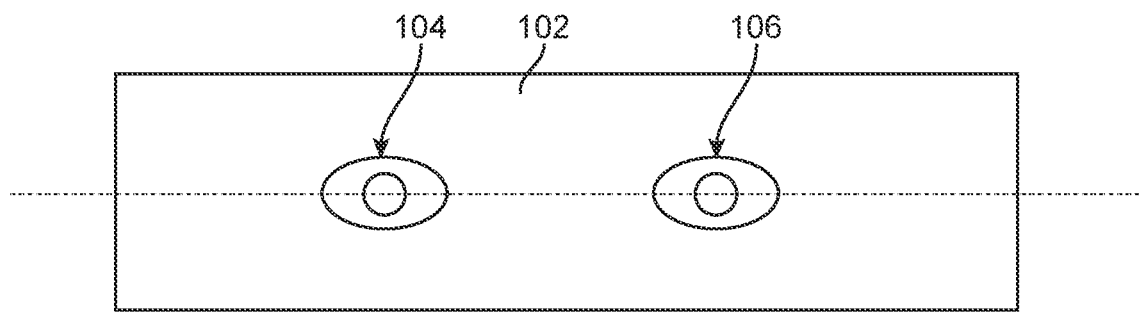
Figure 15B:
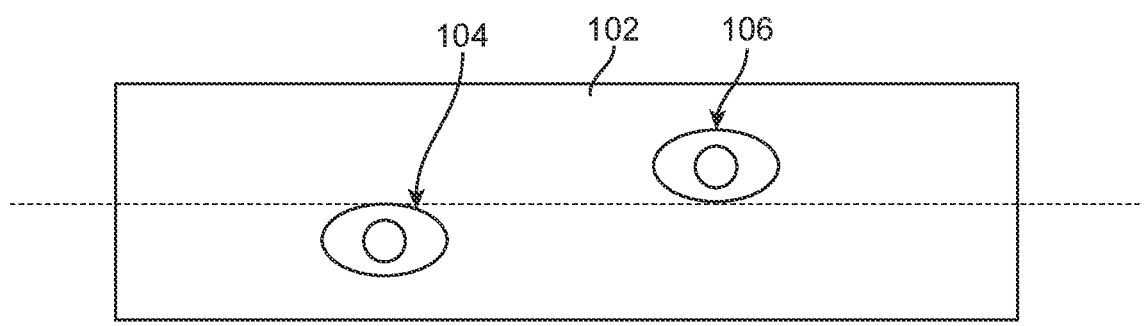
Figure 15C:
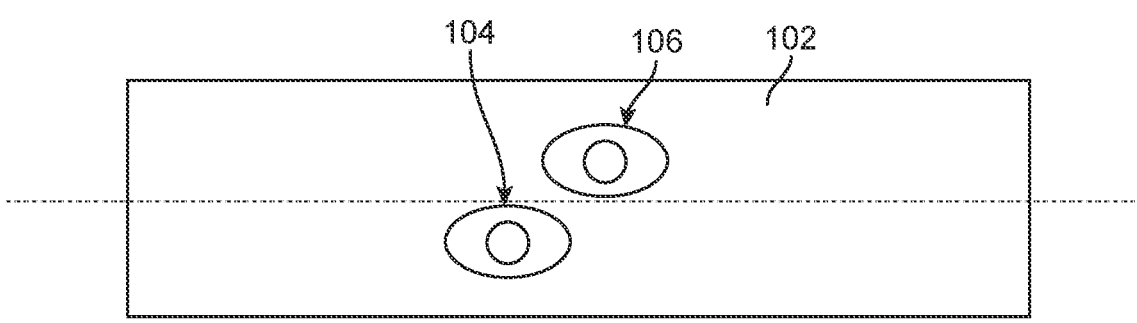

With reference to FIGS. 15A-15C, example top plan views of several stent devices are shown. The couplings 104, 106 in these examples are shown as mobile external couplings (MECs). Due to shape and material, the MECs allows for significant flexibility in aligning the stent-graft with a branch vessel because the top of the MECs when deployed can move longitudinally relative to the longitudinal axis of the main body 102. In particular, the MECs includes an unsupported portion of graft material extending below the support wireform to the base. Stated another way, the MECs are unsupported between the crowns and main stent-graft. The unsupported portion of the graft material does not have any inherent ability to urge the top of the MECs into the ostium of a target branch vessel. However, the support wireform imparts structural integrity to the top of the MECs to properly orient the distal end of MECs towards the ostium and to further prevent the MECs from collapsing or everting into the main body 102 when released from a sleeve of the delivery system during delivery and deployment at the target site. Accordingly, if the stent device is not perfectly aligned with a branch vessel, the MECs can move or shift to cause the top to align with and/or extend into the branch vessel. The mobility of MECs thus reduces the requirement of precise targeting of the ostium while still allowing for perfusion of the branch vessel. See a discussion of MECs in Bruszewski et al., U.S. Pat. No. 9,839,542, issued Dec. 12, 2017, which is herein incorporated by reference in its entirety.

Each MEC may have an outer periphery and a more central opening, with graft material in between. The graft material between the opening and the outer periphery may allow the opening to move within the plane of the opening (e.g., an X-Y plane) and/or in the axis of the opening (e.g., Z plane). In each figure, the dashed line represents a center line at a top/cranial portion of the device. If the cross-section of the device were to be represented as a clock, it would represent the 12 o'clock position.

In the example of FIG. 15A, both couplings 104, 106 are shown on the center line. However, one or both of the couplings 104, 106 may be circumferentially rotated away from the center line, or "clocked" from the center line. In one embodiment, either or both couplings 104, 106 may be clocked from the centerline by up to 30 degrees, such as 5 to 25 degrees, 5 to 20 degrees, or 5 to 15 degrees. In the example shown in FIG. 15B, the couplings 104, 106 are clocked in opposite directions, however, both may be clocked in the same direction. With reference to FIG. 15C, the two couplings 104, 106 may be clocked relative to each other and also axially overlapping. The axial overlap may include overlapping of the outer periphery of the MECs and does not necessarily require that the openings axially overlap. The mobility of the MECs in the lateral vertical direction combined with the pre-wiring of the couplings and the target vessels may allow for the condensed axially overlapping configuration of FIG. 15C. Without one or both of those features, finding and deploying a bridging stent graft into such close together couplings may be very difficult or impossible. However, such a tight axial distance is not unusual for the ostia of the great vessels in many patient anatomies. Therefore, the features disclosed herein may allow for a stent device with closer couplings that would otherwise be very difficult or impossible to deploy.

While embodiments shown herein include two couplings, different numbers of couplings are also contemplated, such as a single coupling or three couplings. For an embodiment with three couplings, guidewires may be pre-wired for the arteries BCA and the LSA couplings (e.g., as described above) and the third coupling may be cannulated via traditional methods. Alternatively, a third through and through guidewire (e.g., guidewire GW4) may be deployed in the artery LCC and the corresponding coupling may be deployed in the same manner as above. For example, the guidewire GW4 could extend from femoral access (or other leg site), through the aorta, into the artery LCC, and exit through the patient's neck. In embodiments where there are three couplings, the axial region of the stent device between the first and third coupling (e.g., arteries BCA and LSA) may be more circumferentially flexible than the other axial regions, similar to described above for two-coupling embodiments. Alternatively, either the axial region between the first and second or the second and third coupling may be more circumferentially flexible than the other regions. In addition, while the above examples have been described with reference to an aortic stent device and deploying bridging stent grafts into the great vessels off the aortic arch, the disclosed devices, systems, and methods can be applied to other catheter-based stent-graft procedures. The pre-wired coupling concept may be applied in any situation or procedure in which a through and through guidewire can be introduced.

This application is related to commonly assigned U.S. patent application Ser. No. 16/502,462, filed Jul. 3, 2019, and issued as U.S. Pat. No. 11,096,775 on Aug. 24, 2021, entitled "SINGLE MULTIBRANCH STENT DEVICE ASSEMBLY AND METHOD", of Perkins et al., which is herein incorporated by reference in its entirety.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A method comprising:
prewiring a first guidewire within a proximal coupling of a single multibranch stent device;
prewiring a second guidewire within a distal coupling of the single multibranch stent device;
the first guidewire extending from the proximal coupling to a tapered tip of a delivery catheter and the second guidewire extending from the distal coupling to the tapered tip;
subsequent to the prewiring the first guidewire and the prewiring the second guidewire, deploying the single multibranch stent device comprising:
deploying a main body within a patient's aorta;
perfusing a brachiocephalic artery through the proximal coupling extending radially from the main body; and
perfusing an aortic branch vessel distal of the brachiocephalic artery through the distal coupling extending radially from the main body, wherein the main body, the proximal coupling, and the distal coupling are permanently coupled to one another.

2. The method of claim 1 further comprising:
deploying a proximal bridging stent graft within the proximal coupling and the brachiocephalic artery.

3. The method of claim 2 wherein the proximal bridging stent graft is located between the main body and a wall of the aorta, wherein the proximal bridging stent graft partially collapses the main body.

4. The method of claim 1 further comprising:
deploying a distal bridging stent graft within the distal coupling and the aortic branch vessel, wherein the distal bridging stent graft is located between the main body and a wall of the aorta, wherein the distal bridging stent graft partially collapses the main body.

5. The method of claim 1 wherein the aortic branch vessel is a left common carotid artery.

6. The method of claim 1 wherein the aortic branch vessel is a left subclavian artery.

7. The method of claim 1 wherein the main body comprises a first longitudinal axis, the proximal coupling comprises a second longitudinal axis extending radially from the first longitudinal axis, and the distal coupling comprises a third longitudinal axis extending radially from the first longitudinal axis.

8. The method of claim 7 wherein the second longitudinal axis is parallel to the third longitudinal axis.

9. The method of claim 7 wherein the second longitudinal axis is radially offset from the third longitudinal axis.

10. The method of claim 1 further comprising coupling a proximal cuff to the main body, the proximal cuff extending proximally from the main body.

11. The method of claim 1 further comprising coupling a distal cuff to the main body, the distal cuff extending distally from the main body.

12. The method of claim 1 wherein the deploying of the single multibranch stent device further comprises: extending the first guidewire in the brachiocephalic artery.

13. The method of claim 12 wherein the deploying of the single multibranch stent device further comprises: extending the second guidewire in the aortic branch vessel.

14. The method of claim 13 further comprising retracting a constraining sheath to free the first guidewire and the second guidewire from the constraining sheath.

15. The method of claim 14 wherein the constraining sheath is further retracted until the proximal coupling is released.

16. The method of claim 15 wherein upon being released, the proximal coupling is misaligned with the brachiocephalic artery, the method further comprising using the first guidewire to align the proximal coupling with the brachiocephalic artery.

17. The method of claim 15 wherein the constraining sheath is further retracted until the distal coupling is released.

18. The method of claim 17 wherein upon being released, the distal coupling is misaligned with the aortic branch vessel, the method further comprising using the second guidewire to align the distal coupling with the aortic branch vessel.

19. The method of claim 1 wherein the proximal coupling and the distal coupling are clocked from a center line at a top portion of the main body.

20. The method of claim 19 wherein the proximal coupling and the distal coupling axially overlap.

21. The method of claim 1 further comprising prewiring a third guidewire within another coupling of the single multibranch stent device.

22. The method of claim 1 wherein the single multibranch stent device is more circumferentially flexible in an axial region between the proximal coupling and the distal coupling than in regions axially outside of the proximal coupling and the distal coupling.

23. The method of claim 22 further comprising rotating the axial region between the proximal coupling and the distal coupling.

24. The method of claim 23 wherein the rotating of the axial region comprises applying force to at least one of the first guidewire and the second guidewire.

25. The method of claim 23 wherein the rotating of the axial region comprises applying torque to the delivery catheter.

\* \* \* \* \*